United States Patent [19]

Diana et al.

[11] Patent Number: 4,857,539
[45] Date of Patent: Aug. 15, 1989

[54] HETEROCYCLIC SUBSTITUTED-PHENOXYALKYLISOX-AZOLES AS ANTIVIRAL USEFUL AGENTS

[75] Inventors: Guy D. Diana, Stephentown; Philip M. Carabateas, Schodack, both of N.Y.

[73] Assignee: Sterling Drug Inc., New York, N.Y.

[21] Appl. No.: 62,803

[22] Filed: Jun. 16, 1987

Related U.S. Application Data

[63] Continuation-in-part of Ser. No. 751,348, Jul. 2, 1985, abandoned, which is a continuation-in-part of Ser. No. 624,302, Jun. 25, 1984, abandoned, which is a continuation-in-part of Ser. No. 527,583, Aug. 29, 1983, abandoned.

[30] Foreign Application Priority Data

Jun. 24, 1986 [CA] Canada .................................. 512258

[51] Int. Cl.$^4$ .................... A61K 31/42; C07D 413/10; C07D 413/12
[52] U.S. Cl. ..................................... 514/378; 548/247; 548/255; 548/336; 548/342; 548/348; 548/352; 548/374; 548/131; 548/143; 548/146; 548/179; 548/203; 548/224; 548/252; 548/560; 548/565; 548/402; 546/275; 546/283; 546/4; 549/60; 549/347; 549/374; 549/472; 549/3; 549/209; 549/66; 514/340; 514/364; 514/368; 514/375; 514/382; 514/359; 514/397; 514/402; 514/406; 514/427; 514/429; 514/444; 514/450; 514/452; 514/461; 556/486; 558/423
[58] Field of Search ........................ 514/378; 548/247

[56] References Cited

U.S. PATENT DOCUMENTS

| | | | |
|---|---|---|---|
| 3,852,056 | 12/1974 | Draber et al. | 548/247 |
| 3,941,800 | 6/1976 | Draber et al. | 548/247 |
| 4,159,336 | 6/1979 | Wright | 514/378 |
| 4,171,365 | 10/1979 | Diana et al. | 514/406 |
| 4,268,678 | 5/1981 | Diana et al. | 548/247 |
| 4,451,476 | 5/1984 | Diana | 424/272 |

FOREIGN PATENT DOCUMENTS 137242  4/1985  European Pat. Off. .

OTHER PUBLICATIONS

Maier et al., Chemical Abstracts, vol. 77, No. 61979n (1972).

Diana et al., Chemical Abstracts, vol. 106, No. 213931y (1987).

*Primary Examiner*—Anton H. Sutto
*Assistant Examiner*—E. Bernhardt
*Attorney, Agent, or Firm*—Thomas L. Johnson; Paul E. Dupont

[57] ABSTRACT

Compounds of the formula

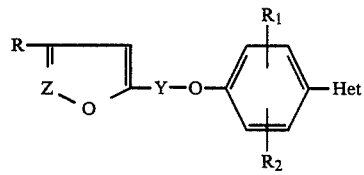

wherein:

Y is an alkylene bridge of 3–9 carbon atoms;

Z is N or HC;

R is hydrogen or lower-alkyl of 1–5 carbon atoms, with the proviso that when Z is N, R is lower-alkyl;

$R_1$ and $R_2$ are hydrogen, halogen, lower-alkyl, lower-alkoxy, nitro, lower-alkoxycarbonyl or trifluoromethyl; and Het is selected from specified heterocyclic groups, are useful and antiviral agents, particularly against picornaviruses, including numerous strains of rhinovirus.

21 Claims, No Drawings

HETEROCYCLIC SUBSTITUTED-PHENOXYALKYLISOXAZOLES AS ANTIVIRAL USEFUL AGENTS

This application is a continuation-in-part of application Ser. No. 751,348, filed July 2, 1985 now abandoned, in turn a continuation-in-part of application Ser. No. 624,302, filed June 25, 1984, now abandoned, in turn a continuation-in-part of application Ser. No. 527,583, filed Aug. 29, 1983, now abandoned.

BACKGROUND OF THE INVENTION (a) Field of the Invention

This invention relates to novel heterocyclic substituted-phenoxyalkylisoxazoles and -furans, to methods for the preparation thereof, and compositions and methods for the use thereof as antiviral agents.

(b) Information Disclosure Statement

Diana U.S. Pat. No. 4,451,476, issued May 29, 1984, discloses antivirally active compounds having the formula

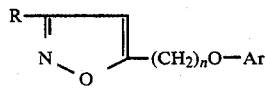

wherein:
R is alkyl of 1 to 3 carbon atoms;
n is an integer from 4 to 8; and
Ar is phenyl or phenyl substituted by one or two substituents selected from the group consisting of halogen, lower-alkyl, lower-alkoxy, nitro, cyano, carboxy, lower-alkoxycarbonyl, lower-alkanoyl, 1-oximino-lower-alkyl, hydrazinocarbonyl, carbamyl and N,N-di-lower-alkylcarbamyl.

Sterling Drug Inc. European Patent Application Publ. No. 137,242, published Apr. 17, 1985, discloses antivirally active compounds having the formula

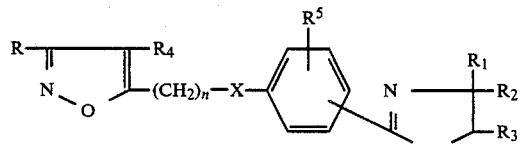

wherein:
R, $R_1$, $R_2$, $R_3$ and $R_4$ are each hydrogen or alkyl of 1 to 3 atoms optionally substituted by hydroxy, lower-alkanoyloxy, lower-alkoxy, chloro, or N=Z, wherein N=Z is amino, lower-alkanoylamino, lower-alkylamino, di-lower-alkylamino, 1-pyrrolidinyl, 1-piperidinyl or 4-morpholinyl; with the proviso that R is other than hydrogen;
$R_5$ is hydrogen, lower-alkyl, halogen, nitro, lower-alkoxy, lower-alkylthio or trifluoromethyl;
X is O or a single bond; and
n is an integer from 3 to 9; and to pharmaceutically acceptable acid-addition salts thereof.

SUMMARY OF THE INVENTION

It has now been found that compounds wherein the oxazoline ring of the compounds of the latter reference is replaced by selected other heterocycles are also effective antiviral agents.

Accordingly, the present invention relates to compounds of the formula

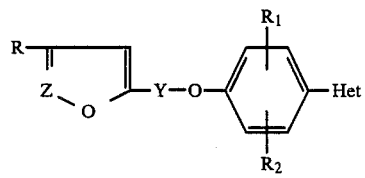

wherein:
Y is an alkylene bridge of 3–9 carbon atoms;
Z in N, or HC or S;
R is hydrogen or lower-alkyl of 1–5 carbon atoms, with the proviso that when Z is N, R is lower-alkyl;
$R_1$ and $R_2$ are hydrogen, halogen, lower-alkyl, lower-alkoxy, nitro, lower-alkoxycarbonyl or trifluoromethyl; and
Het is selected from the group consisting of:

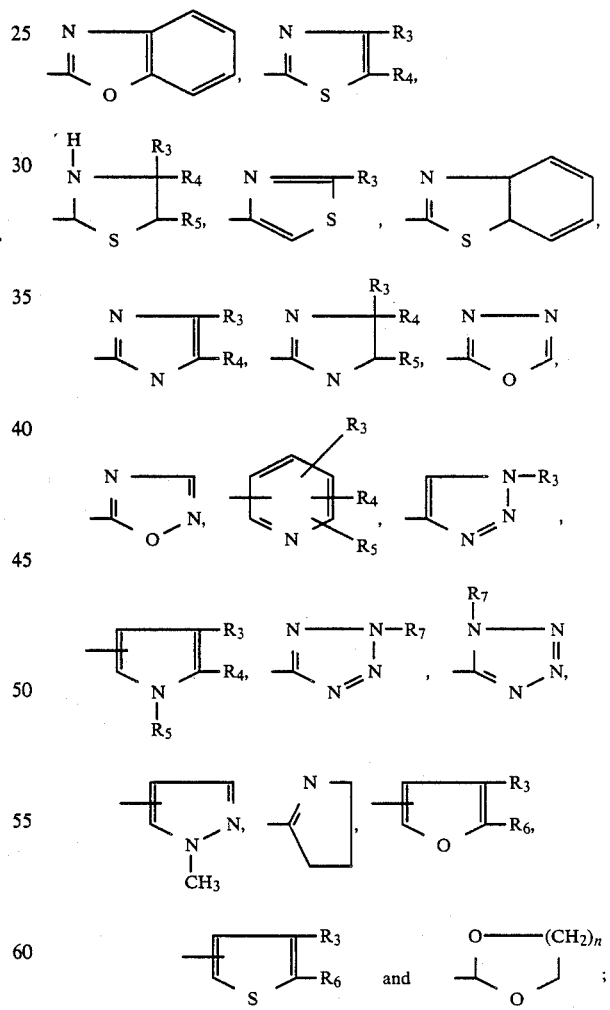

where n is 2 or 3; and
$R_3$, $R_4$ and $R_5$ are hydrogen or lower-alkyl of 1–5 carbon atoms;
$R_6$ is hydrogen, lower-alkyl of 1–5 carbon atoms or chloro;

$R_7$ is hydrogen, or alkyl or hydroxyalkyl of 1-5 carbon atoms;

or pharmaceutically acceptable acid-addition salts of basic members thereof.

A preferred class of compounds within the scope of Formula I are those of the formula

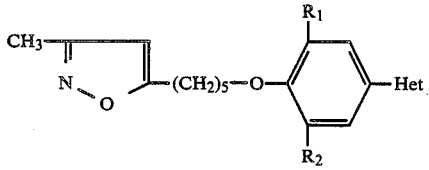

The invention also relates to compositions for combating viruses comprising an antivirally effective amount of a compound of Formulas I or II in admixture with a suitable carrier or diluent, and to methods of combating viruses therewith, including the systemic treatment of viral infections in a mammalian host.

DETAILED DESCRIPTION INCLUSIVE OF PREFERRED EMBODIMENTS

The compounds of Formula I where Het is a nitrogen-containing heterocyclic group are sufficiently basic to form stable acid-addition salts with strong acids, and said salts are within the purview of the invention. The nature of the acid-addition salt is immaterial, provided it is derived from an acid the anion of which is essentially non-toxic to animal organisms. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like.

When the term halogen is used to define the substituents $R_1$ and $R_2$, any of the four common halogens, fluorine, chlorine, bromine or iodine are contemplated; and the term lower-alkoxycarbonyl refers to such groups having from two to four carbon atoms.

The compounds of Formula I can be prepared by a process which comprises reacting a compound of the formula

wherein Hal is chlorine, bromine or iodine, with an alkali metal salt of a compound of the formula

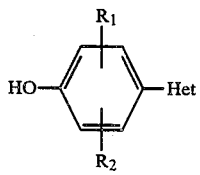

The compounds of Formula I can also be prepared by an alternative process which comprises reacting a compound of the formula

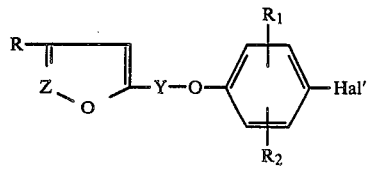

where Hal' is bromine or iodine, with a compound of the formula $$(R')_3Sn\text{-Het}' \qquad \text{VI}$$

where R' is lower-alkyl of 1-6 carbon atoms, and Het' is any of the aromatic type heterocyclic groups included in the definition of Het in Formula I; in the presence of a palladium complex catalyst.

The process for the preparation of compounds of Formula I by reacting intermediates of Formulas III and IV takes place by heating the reactants in an inert solvent in the presence of an alkali metal base, e.g. potassium carbonate or potassium hydroxide at a temperature between about 50° C. and 150° C.

The intermediates of Formula III where Z in N are prepared by reacting an alkali metal derivative of an isoxazole of the formula

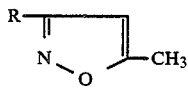

with a dihalide, Hal-Y'-Hal, where Y' is an alkylene bridge of 2 to 8 carbon atoms. Said alkali metal derivative is prepared in situ by treating the compound of Formula VII with an organo-alkali metal base under anhydrous conditions. Preferred organo-alkali metal bases are butyllithium and lithium diisopropylamide.

The intermediates of Formula III where Z in HC are prepared from the appropriate omega-(2-furan)alkanoic acid by reduction to the corresponding alcohol and replacement of the hydroxy group by halogen; or by direct alkylation of furan with a dihalide, Hal-Y-Hal, in the presence of a strong base such as butyllithium.

The intermediates of Formula IV are a generically known class of heterocyclic substituted phenols, prepared as described hereinafter in the general description and specific examples.

In the alternative process comprising reacting compounds of Formulas V and VI, the process is carried out using approximately equimolar amounts of the reactants in an inert solvent at a temperature between about 50° C. and 100° C., conveniently at the reflux temperature of the solvent. The reaction is complete in a period ranging from 5-24 hours. The palladium complex catalyst, present to the extent of about 5 mole percent, can be any such catalyst known to effect cross-coupling of organotin compounds with organic halides [cf. Kosugi et al., Bull. Chem. Soc. Japan 59, 677-679 (1986)], for example $PdCl_2\text{-}(PPh_3)_2$, $Pd(PPh_3)_4$, $PdCl_2[P(o\text{-tolyl})_3]_2$, $PdCl_2 + 2P(OEt)_3$ and $PdCl_2(PhCN)_2$. A preferred catalyst is dichlorobis-(triphenylphosphine)palladium [$PdCl_2(PPh_3)_2$].

The intermediates of Formula V are prepared by reacting an alkali metal salt of a phenol of the formula

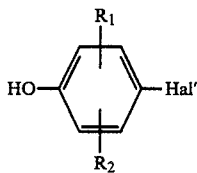

VIII with a compound of Formula III in a procedure analogous to that of the reaction of III with IV.

The organotin reagent of Formula VI is prepared by known procedures comprising reacting a tri-lower-alkyltin halide with an unsubstituted aromatic heterocycle in the presence of a strong base such as butyllithium under anhydrous conditions. The trialkyltin moiety enters the most reactive position on the heterocyclic ring; however, the trialkyltin moiety can be directed to other positions on the heterocyclic ring by using the appropriate halo-substituted heterocycle.

Certain compounds of the invention can be prepared by construction of the Het ring from intermediates having a cyano or formyl group on the phenyl ring, as follows.

The compounds of Formula I where Het is a 4,5-dihydro-1H-imidazolyl group:

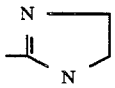

are prepared from the corresponding cyanophenyl compounds of the formula

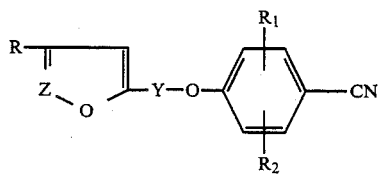

IX by heating the latter with ethylenediamine in acid medium. The compounds of Formula IX are in turn prepared from the appropriate cyanophenol and a compound of Formula III.

The compounds of Formula I where Het is a 2-thiazolyl group:

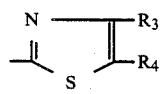

are prepared from the corresponding cyanophenyl compounds of Formula IX by conversion of the latter to the corresponding thioamide with hydrogen sulfide in pyridine, and then reacting the thioamide with a haloalkanone, $R_3CH(Hal)—CO—R_4$.

The compounds of Formula I where Het is a tetrazole group:

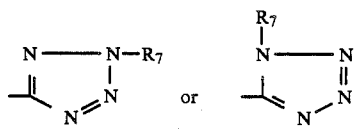

are prepared from the corresponding cyanophenyl compounds of Formula IX by reaction of the latter with sodium azide to give a tetrazole when $R_7$ is hydrogen. Treatment of the latter with a lower-alkyl halide or hydroxy-lower-alkyl halide in the presence of a base gives both isomeric tetrazoles where $R_7$ is lower-alkyl or hydroxy-lower-alkyl.

The compounds of Formula I where Het is a group of the formula

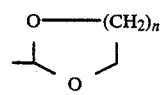

are prepared by conventional cyclic acetal formation by reacting a benzaldehyde derivative of the formula

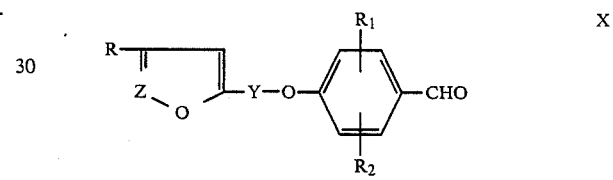

X with ethylene glycol or propylene glycol. The compounds of Formula X are in turn prepared by reacting the appropriate 4-hydroxybenzaldehyde with a compound of Formula III.

The compounds of Formula I where Het is a 2-thiazolidinyl group:

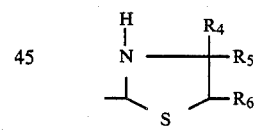

are prepared by reacting a benzaldehyde derivative of Formula X with an amino alkanethiol, $H_2N-C(R_4R_5)CH(R_6)-SH$, heated in a non-polar organic solvent with an acid catalyst.

The compounds of Formula I where Het is a 4-triazolyl group:

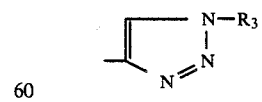

are prepared by reacting a cyanophenyl compound of the Formula IX with the lithium derivative of a N-nitrosoamine, $R_3(CH_3)N—N=O$ according to the procedure of Seebach et al., Angew. Chem., International Ed. 11, 1102 (1972).

The compounds of Formula I where Het is a 4,5-dihydro-3H-pyrrol-2-yl group:

can be prepared by reacting a compound of Formula V with 1-trimethylsilylpyrrolidin-2-one according to the procedure described by Feringa and Jansen, Tetrahedron Letters 507 (1986).

The structure of the compounds of the invention were established by the modes of synthesis, by elementary analysis, and by infrared and nuclear magnetic resonance spectra.

The following examples will further illustrate the invention.

EXAMPLE 1

(a) 2,6-Dichloro-4-iodophenyl trimethylsilyl ether.

A mixture of 5.25 g 2,6-dichloro-4-iodophenol and 2.0 ml (1 equiv.) di(trimethylsilyl)amine was heated at reflux for 3 hrs. The resulting trimethyl silyl ether, obtained in essentially quantitative yield, was used in the next reaction without further purification.

(b) 2,6-Dichloro-4-(2-thienyl)phenol [IV; $R_1$ and $R_2$=Cl, Het=2-thienyl].

To a solution of 1.7 g thiophene in 20 ml ether at 0° C. under nitrogen was added 1.9 ml 10.5M n-butyllithium. The mixture was kept at room temperature for 1 hr and then cooled to −20° C. Cuprous iodide (3.8 g) was then added, and the mixture was allowed to warm to 0° C. and the solvent removed in vacuo. To the residue was added 20 ml dry pyridine and 7.2 ml 2,6-dichloro-4-iodophenyl trimethylsilyl ether. The mixture was heated at reflux for 3.5 hrs and the product isolated and purified by flash filtration (5:1 hexane:ethyl acetate, silica gel) to give 2.3 g (47%) 2,6-dichloro-4-(2-thienyl)-phenol as a yellow solid.

(c) 5-{5-[2,6-Dichloro-4-(2-thienyl)phenoxy]pentyl}-3-methylisoxazole [II; $R_1$ and $R_2$=Cl, Het=2-thienyl].

A solution of 2.3 g 2,6-dichloro-4-(2-thienyl)-phenol, 2.2 g 5-(5-bromopentyl)-3-methylisoxazole and 0.7 g potassium hydroxide in 50 ml acetonitrile was heated at reflux for 5 hrs. Filtration, concentration and flash chromatography (4:1 hexane:ethyl acetate) provided 4.3 g of a light yellow oil which was recrystallized from isopropyl acetate-hexane to give 1.8 g (49%) 5-{5-[2,6-dichloro-4-(2-thienyl)phenoxy]pentyl}-3-methylisoxazole, pale-yellow solid, m.p. 45-47° C. upon further recrystallization from isopropyl acetate-hexane.

The intermediate 5-(5-bromopentyl)-3-methylisoxazole was prepared according to known methods from 1,4-dibromobutane and the lithium salt of 3,5-dimethylisoxazole produced in situ with n-butyllithium and diisopropylamine in tetrehydrofuran solution.

It is contemplated that the 5-(5-bromopentyl)-3-methylisoxazole can be replaced by the homologous 5-(3-bromopropyl)-3-methylisoxazole, 5-(7-bromoheptyl)-3-methylisoxazole or 5-(9-bromononyl)-3-methylisoxazole to give respectively 5-{3-[2,6-dichloro-4-(2-thienyl)phenoxy]propyl}-3-methylisoxazole [I; Y=$(CH_2)_3$, Z=N, R=$CH_3$, $R_1$=2-Cl, $R_2$=6-Cl, Het=2-thienyl], 5-{7-[2,6-dichloro-4-(2-thienyl)-phenoxy]heptyl}-3-methylisoxazole [I; Y=$(CH_2)_7$, Z=N, R=$CH_3$, $R_1$=2-Cl, $R_2$=6-Cl, Het=2-thienyl], or 5-{9-[2,6-dichloro-4-(2-thienyl)phenoxy]-nonyl}-3-methylisoxazole [I; Y=$(CH_2)_9$, Z=N, R=$CH_3$, $R_1$=2-Cl, $R_2$=6-Cl, Het=2-thienyl].

It is further contemplated that 2,6-dichloro-4-(2-thienyl)phenol can be caused to react with 2-(5-bromopentyl)furan (prepared from furan and 1,5-dibromopentane) in accordance with the procedure of Example 1(c) to give 2-{5-[2,6-dichloro-4-(2-thienyl)-phenoxy]pentyl}furan [I; Y=$(CH_2)_5$, Z=HC, R=$CH_3$, $R_1$=2-Cl, $R_2$=6-Cl, Het =2-thienyl].

EXAMPLE 2

5-{5-[4-(2-Furanyl)phenoxy]pentyl}-3-methylisoxazole [II; $R_1$ and $R_2$=H, Het=2-furanyl] was prepared from 3.6 g 4-(2-furanyl)phenol (m.p. 128–129° C., King and Walton, Synthesis 1976, p. 40), 5.4 g 5-(5-bromopentyl)-3-methylisoxazole and 1.5 g potassium hydroxide in acetonitrile according to the procedure of Example 1, part (c), and was obtained (4.2 g) as a light-tan solid, m.p. 86–88° C. when recrystallized from isopropyl acetate.

EXAMPLE 3

(a) 2,6-Dichloro-4-(2-furanyl)phenol [IV; $R_1$=2-Cl, $R_2$=6-Cl, Het=2-furanyl] was prepared from 2,6-dichloro-4-iodophenyl trimethylsilyl ether and furan according to the procedure of Example 1(b), and was obtained in 52% yield as a light brown solid, m.p. 68–70° C.

(b) 5-{5-[2,6-Dichloro-4-(2-furanyl)phenoxy]pentyl}-3-methylisoxazole [II; $R_1$ and $R_2$=Cl, Het=2-furanyl] was prepared from 2,6-dichloro-4-(2-furanyl)phenol and 5-(5-bromopentyl)-3-methylisoxazole according to the procedure of Example 1(c), and was obtained in about 40% yield as a pale-yellow oil which could be caused to crystallize from isopropyl acetate-hexane as a pale-yellow solid, m.p. 29–30° C.

EXAMPLE 4

3-Methyl-5-{5-[4-(1,3,4-oxadiazol-2-yl)phenoxy]pentyl}-isoxazole [II; $R_1$ and $R_2$=H, Het=2-(1,3,4-oxaiazolyl)].

A mixture of 23.6 g 4-(1,3,4-oxadiazolyl)phenol (U.S. Pat. No. 4,218,458, Example XIX), 35 g 5-(5-bromopentyl)-3-methylisoxazole and 40 g milled potassium carbonate in 1.5 liters acetonitrile under nitrogen was heated to reflux. A catalytic amount of sodium iodide was added and refluxing continued for 4 hrs. The reaction mixture was filtered and concentrated to a solid residue. The latter was dissolved in ethyl acetate and the solution washed with water and saturated sodium chloride solution, dried over magnesium sulfate and concentrate in vacuo. The residue was recrystallized from triethylamine to give 18.5 g 3-methyl-5-{5-[4-(1,3,4-oxadiazol-2-yl)phenoxy]-pentyl}isoxazole, white needles, m.p. 84–86° C.

EXAMPLE 5

(a) 4-(2-Thienyl)phenol [IV; $R_1$ and $R_2$=H, Het=2-thienyl].

To a solution of 8.80 g (2-(4-methoxyphenyl)thiophene (prepared from 2-thienylmagnesium bromide and p-iodoanisole) and 5.4 ml propanethiol in 100 ml dry dimethylformamide was carefully added 7.00 g 35% potassium hydride in mineral oil. The reaction mixture was heated at reflux under nitrogen for 16 hours. Isolation of the resulting product afforded after crystallization 2.42 g 4-(2-thienyl)phenol as a yellow powder.

(b) 3-Methyl-5-{5-(4-(2-thienyl)phenoxy]pentyl}isoxazole [II; $R_1$ and $R_2$=H, Het=2-thienyl] was prepared from 2.42 g 4-(2-thienyl)phenol and 5-(5-bromopentyl)-3-methylisoxazole according to the procedure of Example 4, and was obtained in 38% yield (1.7 g) as an off-white solid, m.p. 105–107° C. (from isopropyl acetate-hexane).

EXAMPLE 6

(a) 2-(4-Methoxyphenyl)-4,5-dimethylthiazole.

To a stirred mixture of 65.1 g (4-methoxy)thiobenzamide and 156 ml ethanol was added dropwise 50.1 g 3-chloro-2-butanone, and the reaction mixture was heated at reflux for 3 hours. An additional 6.1 g 2-chloro-3-butanone was added and heating was continued for an additional hour. The reaction mixture was cooled, 300 ml ether added, and the solid which precipitated was collected and dried to give 74.5 g 2-(4-methoxyphenyl)-4,5-di-methylthiazole in the form of its hydrochloride monohydrate, m.p. 166–170° C.

(b) 4-(4,5-Dimethyl-2-thiazolyl)phenol [IV; $R_1$ and $R_2$=H, Het=(4,5-dimethyl-2-thiazolyl)].

The product of part (a) (70.7 g) was added to 470 g pyridine saturated with hydrogen chloride gas, and the mixture was heated 2 hours at reflux. The reaction mixture was poured into 3000 ml ice-water, made basic with ammonium hydroxide, and the solid product was collected. The latter was purified by recrystallization from toluene to give 38.8 g 4-(4,5-dimethyl-2-thiazolyl)phenol, m.p. 194–195° C.

(c) 3-Methyl-5-{5-[4-(4,5-dimethyl-2-thiazolyl)phenoxy]-pentyl}isoxazole [II; $R_1$ and $R_2$=H, Het=(4,5-dimethyl-2-thiazolyl)] was prepared from 2.0 g 4-(4,5-dimethyl-2-thiazolyl)phenol and 2.3 g 5-(5-bromopentyl)-3-methylisoxazole according to the procedure of Example 4: yield 2.5 g, m.p. 96–97° C. (yellow to orange crystals from ethyl acetate).

EXAMPLE 7

(a) 2-(4-Hydroxyphenyl)benzothiazole [IV; $R_1$ and $R_2$=H, Het=benzothiazol-2-yl].

A mixture of 3.7 g 2-aminothiophenol, 4.2 g 4-hydroxybenzoic acid, 4.5 g phosphorus pentoxide and 45 g methanesulfonic acid was stirred for one hour at room temperature and then heated at 90° C. for 10 hours. The reaction mixture was poured slowly into 750 ml 5% sodium bicarbonate solution. The solid which precipitated was collected and dried to give 7.0 g 2-(4-hydroxyphenyl)-benzothiazole.

(b) 2-{4-[[5-(3-Methyl-5-isoxazolyl)pentyl]oxy]-phenyl}-benzothiazole [II; $R_1$ and $R_2$=H, Het=benzothiazol-2-yl] was prepared from 5 g 2-(4-hydroxyphenyl)benzothiazole and 5.1 g 5-(5-bromopentyl)-3-methylisoxazole according to the procedure of Example 4: yield 6.9 g, m.p. 120–121° C. when recrystallized from triethylamine and then from isopropyl acetate.

EXAMPLE 8

(a) 4-(2-Benzothiazolyl)-2-nitrophenol [IV; $R_1$=2-$NO_2$, $R_2$=H, Het=benzothiazol-2-yl].

A mixture of 14.8 g 2-aminothiophenol, 21.6 g 4-hydroxy-3-nitrobenzoic acid, 18 g phosphorus pentoxide and 180 g methanesulfonic acid was heated at 90° C. for 10 hours. The reaction mixture was brought to pH 5 by addition of sodium bicarbonate and sodium hydroxide solutions, and the solid product collected. The latter was recrystallized first from ethyl acetate and then from acetonitrile to give 6.5 g of the above-indicated product, orange-brown needles, m.p. 214–215° C.

(b) 5-{5-[4-(2-Benzothiazolyl)-2-nitrophenoxy]pentyl}-3-methylisoxazole [II; $R_1$=$NO_2$, $R_2$=H, Het=benzothiazol-2-yl] can be prepared by reacting 4-(2-benzothiazolyl)-2-nitrophenol with 5-(5-bromopentyl)-3-methylisoxazole in accordance with the procedure of Example 4.

EXAMPLE 9

5-{5-[4-(2-Benzoxazolyl)phenoxy]pentyl}-3-methylisoxazole [II: $R_1$ and $R_2$=H, Het=benzoxazol-2-yl] was prepared from 5 g 2-(4-hydroxyphenyl)benzoxazole (prepared by heating 4-hydroxybenzamide with 2-aminophenol) and 11.1 g 5-(5-bromopentyl)-3-methylisoxazole according to the procedure of Example 4. There was obtained 5.35 g of the above-indicated product, m.p. 96–98° (from isopropyl acetate).

EXAMPLE 10

(a) 3,5-Dichloro-4-hydroxybenzoic acid hydrazide.

A mixture of 10.0 g methyl 3,5-dichloro-4-hydroxybenzoate and 15 ml hydrazine hydrate was warmed on a steam bath for 3 hrs. Excess hydrazine was removed in vacuo and the residue recrystallized from 2-propanol-water (80:20) to give 9 g of the hydrazide, used directly in the next reaction.

(b) 2,6-Dichloro-4-(1,3,4-oxadiazol-2-yl)phenol [IV; $R_1$=2-Cl, $R_2$=6-Cl, Het=1,3,4-oxadiazol-2-yl].

A mixture of 8.9 g 3,5-dichloro-4-hydroxybenzoic acid hydrazide and 500 ml triethyl orthoformate was stirred and heated at reflux for 4 hrs. The solvent was removed in vacuo to afford the product (9.9 g) as a yellow solid, used directly in the next reaction.

(c) 5-{5-[3,5-Dichloro-4-(1,3,4-oxadiazol-2-yl)phenoxy]-pentyl}-3-methylisoxazole [II; $R_1$ and $R_2$=Cl, Het=1,3,4-oxadiazol-2-yl] was prepared from 8.5 g 2,6-dichloro-4-(1,3,4-oxadiazol-2-yl)phenol and 20 g 5-(5-bromopentyl)-3-methylisoxazole according to the procedure of Example 4, and ws obtained in 34% yield (4.8 g), m.p. 73–74° C. when recrystallized from triethylamine.

It is further contemplated that 4-(1,2,4-oxadiazol-5-yl)phenol or 4-($\Delta^1$-pyrrolin-2-yl)phenol can be caused to react with 5-(5-bromopentyl)-3-methylisoxazole according to the procedure of Example 4 to give, respectively, 5-{5-[4-(1,2,4-oxadiazol-5-yl)phenoxy]pentyl}-3-methylisoxazole [II; $R_1$ and $R_2$=H, Het=1,2,4-oxadiazol-5-yl], or 5-{5-[4-($\Delta^1$-pyrrolin-2-yl)phenoxy]pentyl}-3-methylisoxazole [II; $R_1$ and $R_2$=H, Het=$\Delta^1$-pyrrolin-2-yl].

EXAMPLE 11

(a) 2-(Trimethylstannyl)furan [VI; R'=$CH_3$, Het'=2-furanyl].

To a solution of 6.8 g furan in 100 ml dry ether at 0° C. under nitrogen was added 10.5 ml 9.5M n-butyllithium. The reaction mixture was heated at reflux for 15 min., then cooled to −30° C. and 19.9 g trimethyltin chloride was added. The reaction mixture was allowed to warm to room temperature and then poured into water. The ether layer was separated, washed with water and passed through an alumina column, eluting with hexane. Removal of the solvent provided 22.2 g (96%) 2-(trimethylstannyl)furan as a pale-yellow liquid.

(b) 5-[5-(2,6-Dimethyl-4-iodophenoxy)pentyl]-3-methylisoxazole [V; Y=(CH$_2$)$_5$,Z=N, R=CH$_3$,R$_1$=2-CH$_3$, R$_2$=6-CH$_3$, Hal'=I] was prepared from 10.0 g 2,6-dimethyl-4-iodophenol, 9.4 g 5-(5-bromopentyl)-3-methylisoxazole and 2.9 g potassium hydroxide in 100 ml acetonitrile by a procedure analogous to that of Example 1(c), and was obtained as a pale-yellow oil (15.0 g, 94%) after chromotography.

(c) Dichlorobis(triphenylphosphine)palladium.

A solution of 1.0 g potassium tetrachloro palladate and 2.4 g triphenylphosphine in 20 ml 95% ethanol was heated at reflux for 3 hrs. The solid product was separated, washed with water, ethanol and pentane, and recrystallized from chloroform to give 1.7 g (79%) dichlorobis(triphenylphosphine)palladium as a bright yellow solid.

(d) 5-{5-[4-(2-Furanyl)-2,6-dimethylphenoxy]pentyl}-3-methylisoxazole [II; R$_1$ and R$_2$=CH$_3$, Het=2-furanyl].

A mixture of 5.7 g 5-[5-(2,6-dimethyl-4-iodophenoxy)pentyl]-3-methylisoxazole, 3.8 g 2-(trimethylstannyl)furan and 0.49 g dichlorobis(triphenylphosphine)palladium in 20 ml tetrahydrofuran was heated at reflux under nitrogen for 5 hrs. The reaction mixture was extracted with ether and the ether extracts washed with water and chromatographed. Elution with 5:1 hexane:ethyl acetate provided 3.0 g of product as a colorless oil. Crystallization from isopropyl acetate-hexane gave 5-{5-[4-(2-furanyl)-2,6-dimethylphenoxy]pentyl}-3-methylisoxazole in the form of a colorless solid, m.p. 52–53° C.

By substituting the 2,6-dimethyl-4-iodophenol in part (b) above by the appropriately substituted 4-iodophenols, it is contemplated that other intermediates of Formula V can be prepared, e.g. 5-[5-(2,6-dibromo-4-iodophenoxy)pentyl]-3-methylisoxazole, 5-[5-(2-trifluoromethyl-4-iodophenoxy)pentyl]-3-methylisoxazole, and 5-[5-(2-methoxycarbonyl-4-iodophenoxy)-pentyl]-3-methylisoxazole; and then caused to react with 2-(trimethylstannyl)furan to produce, respectively, 5-{5-[2,6-dibromo-4-(2-furanyl)-phenoxy]pentyl}-3-methylisoxazole, 5-{5-[4-(2-furanyl)-2-trifluoromethylphenoxy]pentyl}-3-methylisoxazole, and 5-{5-[4-(2-furanyl)-2-methoxycarbonylphenoxy]pentyl}-3-methylisoxazole.

EXAMPLE 12

(a) 5-[5-(2,6-Dichloro-4-iodophenoxy)pentyl]-3-methylisoxazole [V; Y=(CH$_2$)$_5$, Z=N, R=CH$_3$, R$_1$=2-Cl, R$_2$=6-Cl, Hal'=I] was prepared in 80% yield from 2,6-dichloro-4-iodophenol and 5-(5-bromopentyl)-3-methylisoxazole, and obtained in the form of a pale-yellow liquid after chromatography.

(b) 5-{5-[2,6-Dichloro-4-(2-furanyl)phenoxy]pentyl}-3-methylisoxazole [II; R$_1$ and R$_2$=Cl, Het=2-furanyl] was prepared from 3.32 g 5-[5-(2,6-dichloro-4-iodophenoxy)-pentyl]-3-methylisoxazole, 2.0 g 2-(trimethylstannyl)furan and 0.26 g dichlorobis(triphenylphosphine)palladium according to the procedure of Example 11(d), and obtained (3.5 g) as a colorless solid, m.p. 29–30° C. (from isopropyl acetate-hexane), identical with the compound of Example 3.

EXAMPLE 13

(a) 5-Methyl-2-(trimethylstannyl)furan [VI; R'=CH$_3$, Het'=5-methyl-2-furanyl] was prepared from 2-methylfuran and trimethyltin chloride according to the procedure of Example 11(a), and was obtained in 88% yield as a pale-yellow liquid.

(b) 5-{5-[2,6-Dimethyl-4-(5-methyl-2-furanyl)-phenoxy]pentyl}-3-methylisoxazole [II; R$_1$ and R$_2$=CH$_3$, Het=5-methyl-2-furanyl] was prepared from 5-[5-(2,6-dimethyl-4-iodophenoxy)pentyl]-3-methylisoxazole (Example 11b) and 5-methyl-2-(trimethylstannyl)furan according to the procedure of Example 11(d), and was obtained in 66% yield as a colorless solid, m.p. 54–55° C. when recrystallized from isopropyl acetate-hexane and ether-hexane.

EXAMPLE 14

5-{5-[2,6-Dichloro-4-(5-methyl-2-furanyl)phenoxy]-pentyl}-3-methylisoxazole [II; R$_1$ and R$_2$=Cl, Het=5-methyl-2-furanyl] was prepared from 5-[5-(2,6-dichloro-4-iodophenoxy)pentyl]-3-methylisoxazole (Example 12a) and 5-methyl-2-(trimethylstannyl)furan (Example 13a) according to the procedure of Example 11(d), and was obtained in 73% yield as a colorless solid, m.p. 51–53° C. (from isopropyl acetate-hexane).

EXAMPLE 15

(a) 3-(Trimethylstannyl)furan [VI; R'=CH$_3$, Het'=3-furanyl].

To a solution of 8.8 g 3-bromofuran in 100 ml ether at −78° C. under nitrogen was added dropwise 6.5 ml 9.5M n-butyllithium. There was then added a solution of 11.93 g trimethyltin chloride in 15 ml ether cooled to −78° C. The reaction mixture after warming to room temperature was filtered and extracted with ether. The ether extracts were dried over potassiusm carbonate, concentrated, and passed through neutral alumina to give 10.3 g (75%) 3-trimethylstannyl)furan as a pale-yellow liquid.

(b) 5-{5-[2,6-Dimethyl-4-(3-furanyl)phenoxy]pentyl}-3-methylisoxazole [II; R$_1$ and R$_2$=CH$_3$, Het=3-furanyl] was prepared from 5-[5-(2,6-dimethyl-4-iodophenoxy)pentyl]-3-methylisoxazole (Example 11b) and 3-(trimethylstannyl)-furan according to the procedure of Example 11(d), and was obtained in 35% yield as a cream-colored solid, m.p. 48–50° C. (from isopropyl acetate-hexane).

EXAMPLE 16

5-{5-[2,6-Dichloro-4-(3-furanyl)phenoxy]pentyl}-3-methylisoxazole [II; R$_1$ and R$_2$=Cl, Het=3-furanyl] was prepared from 5-[5-(2,6-dichloro-4-iodophenoxy)-pentyl]-3-methylisoxazole (Example 12a) and 3-(trimethylstannyl)-furan (Example 15a) according to the procedure of Example 11(d), and was obtained in 67% yield as a pale-orange solid, m.p. 37–39° C. (from isopropyl acetate-hexane).

EXAMPLE 17

(a) 2-(Tributylstannyl)thiophene [VI; R'=(CH$_2$)$_3$CH$_3$, Het'=2-thienyl] was prepared from thiophene and tri(n-butyl)-tin chloride according to the procedure of Example 11(a), and was obtained in essentially quantitative yield as a pale-yellow oil.

(b) 5-{5-[2,6-Dimethyl-4-(2-thienyl)phenoxy]pentyl}-3-methylisoxazole [II; R$_1$ and R$_2$=Cl, Het=2-thienyl]

was prepared from 5-[5-(2,6-dimethyl-4-iodophenoxy)-pentyl]-3-methylisoxazole (Example 11b) and 2-(tributylstannyl)thiophene according to the procedure of Example 11(d) and was obtained in 57% yield as a pale-yellow solid, m.p. 45–47° C. (from isoproply acetate-hexane).

EXAMPLE 18

5-{5-[2,5-Dichloro-4-(2-thienyl)phenoxy]pentyl}-3-methylisoxazole [II; $R_1$ and $R_2$=Cl, Het=2-thienyl] was prepared from 5-[5-(2,6-dichloro-4-iodophenoxy)-pentyl]-3-methylisoxazole (Example 12a) and 2-(tributylstannyl)thiohene (Example 17a) according to the procedure of Example 11(d), and was obtained in 76% yield as a colorless solid, m.p. 50–52° C. (from isopropyl acetate-hexane). This compound is identical with the compound of Example 1(c).

EXAMPLE 19

(a) 5-Methyl-2-(trimethylstannyl)thiophene [VI; R'=CH$_3$, Het'=5-methyl-2-thienyl] was prepared from 2-methylthiophene and trimethyltin chloride according to the procedure of Example 11(a) and was obtained in 89% yield as a pale-yellow oil, $n_D^{22}$=1.5385.

(b) 5-{5-[2,6-Dimethyl-4-(5-methyl-2-thienyl)phenoxy]pentyl}-3-methylisoxazole [II; $R_1$ and $R_2$=CH$_3$, Het=5-methyl-2-thienyl] was prepared from 5-[5-(2,6-dimethyl-4-iodophenoxy)pentyl]-3-methylisoxazole (Example 12a) and 5-methyl-2-(trimethylstannyl)thiophene according to the procedure of Example 11(d), and was obtained in about 40% yield as an off-white solid, m.p. 64.5 –65.5 ° C. (from hexane).

EXAMPLE 20

(a) 5-Methyl-2-(tributylstannyl)thiophene [VI; R'=(CH$_2$)$_3$CH$_3$, Het'=5-methyl-2-thienyl] was prepared from 2-methylthiophene and tri(n-butyl)tin chloride according to the procedure of Example 11(a), and was obtained in 97% yield as a colorless liquid.

(b) 5-{5-[2,6-Dichloro-4-(5-methyl-2-thienyl)phenoxy]pentyl}-3-methylisoxazole [II $R_1$ and $R_2$=Cl, Het=5-methyl-2-thienyl] was prepared from 5-[5-(2,6-dichloro-4-iodophenoxy)pentyl]-3-methylisoxazole (Example 12a) and 5-methyl-2-(tributylstannyl)thiophene according to the procedure of Example 11(d), and was obtained in about 45% yield as a colorless solid, m.p. 43–45° C. (from isopropyl acetate-hexane).

EXAMPLE 21

(a) 3-(Trimethylstannyl)thiophene [VI; R'=CH$_3$, Het'=3-thienyl] was prepared from 3-bromothiophene and trimethyltin chloride according to the procedure of Example 15(a), and was obtained in 93% yield as a pale-yellow liquid.

(b) 5-{5-[2,6-Dimethyl-4-(3-thienyl)phenoxy]pentyl}-3-methylisoxazole [II; $R_1$ and $R_2$=CH$_3$, Het=3-thienyl] was prepared from 5-[5-(2,6-dimethyl-4-iodophenoxy)pentyl]-3-methylisoxazole (Example 11b) and 3-(trimethylstannyl)-thiophene according to the procedure of Example 11(d), and was obtained in 47% yield as a colorless solid, m.p. 53–54° C. (from isopropyl acetate-hexane).

EXAMPLE 22

5-{5-[2,6-Dichloro-4-(3-thienyl)phenoxy]pentyl}-3-methylisoxazole [II; $R_1$ and $R_2$=Cl, Het=2-thienyl] was prepared from 5-[5-(2,6-dichloro-4-iodophenoxy)pentyl]-3-methylisoxazole (Example 12a) and 3-(trimethylstannyl)-thiophene (Example 21a) according to the procedure of Example 11(d), and was obtained in 84% yield as a colorless solid, m.p. 43–44° C. (from isopropyl acetate-hexane).

EXAMPLE 23

(a) 1-Methyl-2-(trimethylstannyl)pyrrole [VI; R'=CH$_3$, Het'=1-methyl-2-pyrrolyl] was prepared from 1-methylpyrrole and trimethyltin chloride according to the procedure of Example 11(a), and was obtained in 76% yield as a light orange oil.

(b) 5-{5-[2,6-Dimethyl-4-(1-methyl-1H-pyrrol-2-yl)phenoxy]-pentyl}-3-methylisoxazole [II; $R_1$ and $R_2$=CH$_3$, Het=1-methylpyrrol-2-yl] was prepared from 5-[5-(2,6-dimethyl-4-iodophenoxy)entyl]-3-methylisoxazole (Example 11b) and 1-methyl-2-(trimethylstannyl)pyrrole according to the procedure of Example 11(d), and was obtained in 25% yield as a clear, viscous amber oil.

EXAMPLE 24

5-{5-[2,6-Dichloro-4-(1-methyl-1H-pyrrol-2-yl)phenoxy]-pentyl}-3-methylisoxazole [II; $R_1$ and $R_2$=Cl, Het=1-methylpyrrol-2-yl] was prepared from 5-[5-(2,6-dichloro-4-iodophenoxy)pentyl]-3-methylisoxazole (Example 12a) and 1-methyl-2-(trimethylstannyl)-pyrrole (Example 23a), according to the procedure of Example 11(d), and was obtained in 89% yield as a colorless solid, m.p. 46–47° C. (from isopropyl acetate-hexane).

EXAMPLE 25

(a) 2-(Trimethylstannyl)pyridine [VI; R'=CH$_3$, Het'=2-pyridinyl] was prepared from 2-bromopyridine and trimethyltin chloride according to the procedure of Example 15(a), and was obtained in 95% crude yield as an orange liquid, $n_D^{23}$=1.5310. Fractionation provided a product with b.p. 74° C. (4.5 mm), $n_D^{22.5}$=1.5356.

(b) 5-{5-[2,6-Dimethyl-4-(2-pyridinyl)phenoxy]pentyl}3-methylisoxazole [II; $R_1$ and $R_2$=CH$_3$, Het=2-pyridinyl] was prepared from 5-[5-(2,6-dimethyl-4-iodophenoxy)pentyl]-3-methylisoxazole (Example 11b) and 2-(trimethylstannyl)pyridine according to the procedure of Example 11(d), and was obtained in about 35% yield as a colorless solid, m.p. 31.5–32.5° C. (from ether-pentane).

EXAMPLE 26

5-{5-[2,6-Dichloro-4-(2-pyridinyl)phenoxy]pentyl}-3-methylisoxazole [II; $R_1$ and $R_2$=Cl, Het=2-pyridinyl] was prepared from 5-[5-(2,6-dichloro-4-iodophenoxy)pentyl]-3-methylisoxazole (Example 12a) and 2-(trimethylstannyl)-pyridine (Example 25a), according to the procedure of Example 11(d), and was obtained in 80% yield as a colorless solid, m.p. 70.5–71.25° C. (from hexane).

EXAMPLE 27

(a) 3-(Trimethylstannyl)pyridine [VI; R'=CH$_3$, Het'=3-pyridinyl] was prepared from 3-bromopyridine and trimethyltin chloride according to the procedure of Example 15(a), and was obtained in 93% crude yield, $n_D^{22}=1.5393$ after fractionation.

(b) 5-{5-[2,6-Dichloro-4-(3-pyridinyl)phenoxy]pentyl}-2-methylisoxazole [II; $R_1$ and $R_2$=Cl, Het=3-pyridinyl] was prepared from 5-[5-(2,6-dichloro-4-iodophenoxy)pentyl]-3-methylisoxazole (Example 12a) and 3-(trimethylstannyl)pyridine, according to the procedure of Example 11(d), and was obtained in about 30% yield as colorless needles, m.p. 84–84.8° C. (from hexane).

EXAMPLE 28

(a) 4-(Trimethylstannyl)pyridine [VI; R'=CH$_3$, Het'=4-pyridinyl] was prepared from 4-bromopyridine and trimethyltin chloride according to the procedure of Example 15(a), and was obtained in 95% crude yield as a liquid, $n_D^{22}=1.5346$. Fractionation at 41° C. (0.06 mm) afforded material with $n_D^{22}=1.5413$.

(b) 5-{5-[2,6-Dimethyl-4-(4-pyridinyl)phenoxy]pentyl }-2-methylisoxazole [II; $R_1$ and $R_2$=CH$_3$, Het=4-pyridinyl] was prepared from 5-{5-(2,6-dimethyl-4-iodophenoxy)pentyl]-3-methylisoxazole and 4-(trimethylstannyl)pyridine, according to the procedure of Example 11(d), and was obtained in about 65% yield as a colorless solid, m.p. 65–65° C. (from hexane).

EXAMPLE 29

5-{5-[2,6-Dichloro-4-(4-pyridinyl)phenoxy]pentyl }-2-methylisoxazole [II; $R_1$ and $R_2$=Cl, Het=4-pyridinyl] was prepared from 5-[5-(2,6-dichloro-4-iodophenoxy)pentyl]-3-methylisoxazole (Example 12a) and 4-(trimethylstannyl)-pyridine (Example 28a), according to the procedure of Example 11(d), and was obtained in 42% yield as an offwhite solid, m.p. 79.5–80° C. (from ether).

By analogous procedures it is contemplated that benzoxazole and benzothiazole can be converted to the respective 2-(trimethylstannyl) derivatives, and the latter caused to react with 5-{5-(2,6-dichloro-4-iodophenoxy)pentyl]-3-methylisoxazole to give, respectively, 5-{5-[2,6-dichloro-4-(benzoxazol-2-yl)phenoxy]pentyl}-3-methylisoxazole [II; $R_1$ and $R_2$=Cl, Het=-benzoxazol-2-yl] and 5-{5-[2,6-dichloro-4-(benzothiazol-2-yl)phenoxy]-pentyl}-3-methylisoxazole [II; $R_1$ and $R_2$=Cl, Het=benzothiazol-2-yl].

EXAMPLE 30

4-(6-Bromohexyloxy)benzonitrile.

A mixture of 23.8 g (0.2 mole) 4-cyanophenol, 55.3 g (0.4 mole milled potassium carbonate, 97.6 g 1,6-dibromohexane, 0.5 g sodium iodide and 750 ml acetone was stirred at reflux for two days. The solid was filtered off and the filtrate concentrated in vacuo. The residue was partitioned between water and methylene dichloride, and the organic phase was dried and concentrated. The residue was distilled to give 40 g 4-(6-bromohexyloxy)-benzonitrile, b.p. 150–160° C.(0.05 mm).

(b) 5-[7-(4-Cyanophenoxy)heptyl]-3-methylisoxazole [IX; Y=(CH$_2$)$_7$, Z=N, R=CH$_3$, $R_1$ and $R_2$=H].

To a suspension of 301 mg lithium wire (¼ inch portions) in 10 ml tetrahydrofuran under nitrogen was added 6.72 ml diisopropylamine and 3.44 ml styrene while maintaining the temperature at 25° C. The mixture was stirred until all the lithium had dissolved (about four hours) and then cooled to −55° C. 3,5-Dimethylisoxazole (4.3 g) in 10 ml tetrahydrofuran was then added dropwise and the mixture stirred for an hour at −55° C. 4-(6-Bromohexyloxy)benzonitrile (12 g) in 10 ml tetrahydrofuran was then added dropwise over a period of one hour, and the mixture was allowed to warm to room temperature and stirred for three days. The solvent was removed in vacuo, the residue treated with 5% ammonium chloride solution and extracted with ether. The ether extracts were dried and concentrated, and the residue subjected to high pressure liquid chromatography with ether-hexane (1:1) mixture to give 3.9 g 5-[7-(4-cyanophenoxy)-heptyl]-3-methylisoxazole, used directly in the next reaction.

(c) 5-{7-[4-(4,5-Dihydro-1H-imidazol-2-yl)phenoxy]heptyl}-3-methylisoxazole [I; Z=N, Het=4-(4,5-dihydro-1H-imidazol-2-yl), R=CH$_3$, $R_1$ and $R_2$=H, Y=(CH$_2$)$_7$].

A mixture of 6.9 g 5-[7-(4-cyanophenoxy)heptyl]-3-methylisoxazole and 11.25 g ethylenediamine mono-p-toluenesulfonate salt was heated at 200° C. for 2 hours. The reaction mixture was cooled and partitioned between chloroform and 10% sodium hydroxide solution. The organic layer was dried (MgSO$_4$) and concentrated in vacuo to afford a solid (4.65 g) which was recrystallized from ethyl acetate to give 5-{7-[4-(4,5-dihydro-1H-imidazol-2-yl)phenoxy]heptyl}-3-methylisoxazole, m.p. 118–119° C. Treatment with hydrogen chloride in 2-propanol solution afforded the monohydrochloride hemihydrate, m.p. 142–144° C.

EXAMPLE 31

(a) 5-[5-(4-Thiocarbamylphenoxy)pentyl]-3-methylisoxazole.

Hydrogen sulfide gas was bubbled through a solution of 17.49 g 5-[5-(4-cyanophenoxy)pentyl]-3-methylisoxazole and 4.5 ml triethylamine in 105 ml pyridine for a two hour period. The reaction mixture was allowed to stand for 20 hours and the solvent was removed in vacuo. The residue was recrystallized from acetonitrile to give 10.2 g 5-[5-(4-thiocarbamylphenoxy)pentyl]-3-methylisoxazole as a yellow solid, m.p. 156–158° C.

(b) 3-Methyl-5-{5-[4-(2-thiazolyl)phenoxy]pentyl}isoxazole [I; Z=N, Het=4-(2-thiazolyl), R=CH$_3$, $R_1$ and $R_2$=H, Y=(CH$_2$)$_5$].

A suspension of 7.5 g 5-[5(4-thiocarbamylphenoxy)-pentyl]-3-methylisoxazole and 24.6 g chloroacetaldehyde (50% in water) in 150 ml absolute ethanol was refluxed for 3.5 hours. The reaction mixture was concentrated in vacuo and the residue recrystallized from ethyl acetate-hexane to give 4.5 g 3-methyl-5-{5-[4-(2-thiazolyl)phenoxy]pentyl}isoxazole, m.p. 78–80° C.

EXAMPLE 32

(a) 5-[5-(2,6-Dichloro-4-cyanophenoxy)pentyl]-3-methylisoxazole [IX; Y=(CH$_2$)$_5$, Z=N, R=CH$_3$, $R_1$=2-Cl, $R_2$=6-Cl] was prepared from 13.4 g 3,5-dichloro-4-hydroxybenzonitrile, 23.2 g 5-(5-bromopentyl)-3-methylisoxazole, 20.7 g potassium carbonate and 15 g sodium iodide in 250 ml dimethylformamide, similar to the procedure of Example 4, and was obtained in the form of colorless crystals (11.6 g), m.p. 59–60° C. (from tertiary-butyl methyl ether-hexane).

(b) 5-[5-(2,6-Dichloro-4-carbamylphenoxy)pentyl]-3-methylisoxazole was prepared from 7.3 g 5-[5-(2,6- dichloro-4-cyanophenoxy)pentyl]-3-methylisoxazole, hydrogen sulfide and 2 ml triethylamine in 100 ml pyridine according to the procedure of Example 31(a), and was obtained in the form of a yellow solid (8.0 g), m.p. 138–140° C.

(c)
5-{5-[2,6-Dichloro-4-(4,5-dimethyl-2-thiazolyl)phenoxy]pentyl}-3-methylisoxazole [II; $R_1$ and $R_2$=Cl, Het=4,5-dimethyl-2-thiazolyl].

A mixture of 3.6 g 5-[5-(2,6-dichloro-4-carbamylphenoxy)pentyl]-3-methylisoxazole and 3.0 g 3-bromo-2-butanone in 50 ml absolute ethanol was heated at reflux for 6 hrs. The reaction mixture was concentrated in vacuo and the residue partitioned between ether and saturated sodium bicarbonate solution. From the ether layer was isolated an orange oil which after chromatography and recrystallization from ether-hexane gave 5-{5-[2,6-dichloro-4-(4,5-dimethyl-2-thiazolyl)phenoxy]pentyl}-3-methylisoxazole as a colorless solid, m.p. 57–58° C.

EXAMPLE 33

5-{5-[2,6-Dichloro-4-(1H-tetrazol-5-yl)phenoxy]pentyl}-3-methylisoxazole [II; $R_1$ and $R_2$=Cl, Het=1H-tetrazol5-yl].

A mixture of 14.7 g 5-[5-(2,6-dichloro-4-cyanophenoxy)pentyl]-3-methylisoxazole (Example 32a), 2.96 g sodium azide and 0.32 g ammonium chloride in 150 ml dimethylformamide was stirred and heated at 100° C. for 24 hrs. The reaction mixture was concentrated in vacuo, and the residue was dissolved in ethyl acetate and washed with 2N hydrochloric acid. The organic layer was dried over magnesium sulfate and concentrated in vacuo to a solid residue. The latter was recrystallized from ethyl acetate to give 10.3 g (62%) 5-{5-[2,6-dichloro-4-(1H-tetrazol-5yl)phenoxy]pentyl}-3-methylisoxazole, m.p. 122–123° C.

EXAMPLE 34

A mixture of 6.4 g 5-{5-[2,6-dichloro-4-(1H-tetrazol-5-yl)phenoxy]pentyl}-3-methylisoxazole (Example 33), 2.8 g methyl iodide and 3.0 g milled potassium carbonate in 200 ml acetonitrile was stirred at room temperature overnight. The reaction mixture was filtered and concentrated in vacuo. The residue was dissolved in ethyl acetate and the solution washed with water, saturated sodium chloride solution, dried over magnesium sulfate and concentrated in vacuo. The residual oil was chromatographed using a hexane-ethyl acetate solvent system. Hexane:ethyl acetate 2:1 eluant brought out a first product which when recrystallized from ether-hexane gave 4.24 g (64%) of 5-{5-[2,6-dichloro-4-(2-methyl-2H-tetrazol-5-yl)phenoxy]pentyl}-3-methylisoxazole [II; $R_1$ and $R_2$=Cl, Het=2-methyl-2H-tetrazol-5-yl], colorless solid, m.p. 47–49° C. Hexane:ethyl acetate 3:2 eluant brought out a second product which when recrystallized from ethyl acetate-hexane gave 890 mg (13%) of 5-{5-[2,6-dichloro-4-(1-methyl-1-H-tetrazol-5-yl)phenoxy]-pentyl}-3-methylisoxazole [II; $R_1$ and $R_2$=Cl, Het=1-methyl-1-H-tetrazol-5-yl], colorless solid, m.p. 75–76° C.

EXAMPLE 35

(a)
4-[5-(3-Methyl-5-isoxazolyl)pentylosxy]benzaldehyde.

A solution of 7.2 g 4-hydroxybenzaldehyde, 14.6 g 5-(5-bromopentyl)-3-methylisoxazole, 4 g potassium hydroxide in 100 ml acetonitrile was heated at reflux for 1.5 hours. The reaction mixture was cooled and filtered the solvent removed, and the residue recrystallized from isopropyl acetate-hexane to give 10.8 g 4-[5-(3-methyl-5-isoxazolyl)pentyloxy]benzaldehyde as a pale-yellow powder.

(b)
5-{5-[4-(1,3-Dioxol-2-yl)phenoxy}-3-methylisoxazole [II; $R_1$ and $R_2$=H, Het=1,3-dioxol-2-yl].

A mixture of 9.03 g 4-[5-(3-methyl-5-isoxazollyl)pentyloxy]benzaldehyde, 2.26 g ethylene glycol and a trace of p-toluenesulfonic acid in 80 ml benzene was heated at reflux using a Dean-Stark trap for 4 hours. The product was isolated and recrystallized from isopropyl acetate-hexane to give 7.08 g 5-{5-[4-(1,3-dioxol-2-yl)-phenoxy]pentyl}-3-methylisoxazole as a pale-yellow solid, m.p. 38–39° C. By replacing the 4-hydroxybenzaldehyde in part (a) above by a molar equivalent amount of 3,5-dichloro-4-hydroxybenzaldehyde and carrying out the steps of parts (a) and (b), there can be obtained 5-{5-[2,6-dichloro-4-(1,3-dioxol-2-yl)phenoxy]pentyl}-3-methylisoxazole [II; $R_1$ and $R_2$=Cl, Het=1,3-dioxol-2-yl].

EXAMPLE 36

3-Methyl-5-{5-[4-(2-thiazolidinyl)phenoxy]pentyl}isoxazole [II; Het=4-(2-thiazolidinyl), R=$CH_3$, $R_1$ and $R_2$=H].

A solution of 4.00 g of 4-[5-(3-methyl-5-isoxazolyl)pentyloxy]benzaldehyde (Example 35a), 1.22 g of 2-aminoethanethiol and a trace of p-toluenesulfonic acid in 30 ml of toluene was heated at reflux for 2 hours using a Dean-Stark trap. The product was isolated and recrystallized from isopropyl acetate-hexane to give 1.93 g of the above-indicated product, m.p. 82–84° C.

EXAMPLE 37

(a) 4-(2-Methyl-4-thiazolyl)phenol.

To a stirred solution of 400 g of 4-acetoxy-α-bromoacetophenone in 900 ml of absolute ethanol was added over a 2 minute period 117 g of thioacetamide, and the reaction mixture was heated at reflux for 2 hours and stirred overnight at room termperature. The solid product was collected to give 360 g of the hydrobromide salt (m.p. 253–257° C.) of the desired product. The latter was dissolved in aqueous methanol and treated with potassium hydroxide solution to produce 2.5 g of 4-(2-methyl-4-thiazolyl)phenol, m.p. 212–214° C.

(b) 3-Methyl-5-{7-[4-(2-methyl-4-thiazolyl)phenoxy]-heptyl}-isoxazole [I; Z=N, Het=4-(2-methyl-4-thiazolyl), $R_1$ and $R_2$=H, Y=$(CH_2)_7$] was prepared from 7.3 g of 4-(2-methyl-4-thiazolyl)phenol and 5-(7-bromoheptyl)-3-methylisoxazole according to the procedure of Example 4: yield 10.6 g, m.p. 100–101° C.

EXAMPLE 38

5-{5-[2,6-Dichloro-4-(4,5-dihydro-3H-pyrrol-2-yl)phenoxy]-pentyl}-3-methylisoxazole [II; $R_1$ and $R_2$=Cl, Het=4,5-dihydro-3H-pyrrol-2-yl].

To a solution of 5.0 g 5-[5-(2,6-dichloro-4-iodophenoxy)pentyl]-3-methylisoxazole (Example 12a) in 75 ml dry ether cooled to −78° C. under nitrogen was added 1.4 ml n-butyllithium (9.5 m). A solution of 1.8 g 1-trimethylsilylpyrrolidin-2-one [cf. Feringa et al., Tetrahedron Letters, 507 (1986)] in ether was then added dropwise. The reaction mixture was allowed slowly to come to room temperature, and was washed with water and dried over potassium carbonate. The product was isolated and chromatographed (3:1 hexane:ethyl acetate) and recrystallized from isopropyl acetate/hexane to give 1.8 g 5-{5-[2,6-dichloro-4-(4,5-dihydro-3H-pyrrol-2-yl)phenoxy]pentyl}-3-methylisoxazole, m.p. 57–59° C.

EXAMPLE 39

5-{5-[4-(4,5-Dihydro-3H-pyrrol-2-yl)-2,6-dimethylphenoxy]pentyl}-3-methylisoxazole [II; $R_1$ and $R_2 = CH_3$, Het=4,5-dihydro-3H-pyrrol-2-yl] was prepared from 7.5 g 5-[5-(2,6-dimethyl-4-iodophenoxy)pentyl]-3-methylisoxazole (Example 11b) and 3.5 g 1-trimethylsilylpyrrolidin-2-one according to the procedure of Example 38, and was obtained (3.05 g) as a colorless solid, m.p. 64–65° C. (from isopropyl acetate/hexane).

The compounds of the following Examples 40–47 were prepared by the general procedure illustrated by Example 11 hereinabove:

EXAMPLE 40

5-{5-[2,6-Dichloro-4-(1-methyl-1H-imidazol-2-yl)phenoxy]pentyl}-3-methylisoxazole [II; $R_1$ and $R_2 = Cl$, Het=1-methyl-1H-imidazol-2-yl] was prepared from 9.4 g 1-methyl-2-(tributylstannyl)imidazole, 11.2 g 5-[5-(2,6-dichloro-4-iodophenoxy)pentyl]-3-methylisoxazole and 0.53 g dichlorobis(triphenylphosphine)palladium, and was obtained (5.08 g) as a clear amber liquid.

EXAMPLE 41

5-{5-[2,6-Dimethyl-4-(1-methyl-1H-imidazol-2-yl)phenoxy]pentyl}-3-methylisoxazole [II; $R_1$ and $R_2 = CH_3$, Het=1-methyl-1H-imidazol-2-yl] was prepared from 11.2 g 1-methyl-2-(tributylstannyl)imidazole, 12.1 g 5-[5-(2,6-dimethyl-4-iodophenoxy)pentyl]-3-methylisoxazole and 0.64 g dichlorobis(triphenylphosphine)palladium, and was obtained (3.74 g) in the form of a colorless solid, m.p. 83–84° C. (from ether).

EXAMPLE 42

5-{5-[2,6-Dimethyl-4-(3-pyridinyl)phenoxy]pentyl}-3-methylisoxazole [II; $R_1$ and $R_2 = CH_3$, Het=3-pyridinyl] was prepared from 9.69 g 3-(trimethylstannyl)pyridine, 15.9 g 5-[5-(2,6-dimethyl-4-iodophenoxy)pentyl]-3-methylisoxazole and 1.4 g dichlorobis(triphenylphosphine)palladium, and was obtained (4.03 g) in the form of a colorless solid, m.p. 53–54° C. (from hexane).

EXAMPLE 43

5-{-[2,6-Dichloro-4-(6-methyl-2-pyridinyl)phenoxy]pentyl}-3-methylisoxazole [II; $R_1$ and $R_2 = Cl$, Het=6-methyl-2-pyridinyl] was prepared from 4.5 g 2-trimethylstannyl-6-methylpyridine, 7.0 g 5-[5-(2,6-dichloro-4-iodophenoxy)pentyl]-3-methylisoxazole and 0.55 g dichlorobis(triphenylphosphine)palladium, and was obtained (5.3 g) as a colorless solid, m.p. 54–55° C. (from isopropyl acetate/hexane).

EXAMPLE 44

5-{5-[2,6-Dimethyl-4-(6-methyl-2-pyridinyl)phenoxy]pentyl}-3-methylisoxazole [II; $R_1$ and $R_2 = CH_3$, Het=6-methyl-2-pyridinyl] was prepared from 7.0 g 2-trimethylstannyl-6-methylpyridine, 100 g 5-[5-(2,6-dimethyl-4-iodophenoxy)pentyl]-3-methylisoxazole and 0.52 g dichlorobis(triphenylphosphine)palladium, and was obtained (1.9 g) as a colorless solid, m.p. 62–64° C. (from isopropyl acetate/hexane).

EXAMPLE 45

5-{5-[4-(5-Chloro-2-furanyl)-2,6-dimethylphenoxy]pentyl}-3-methylisoxazole [II; $R_1$ and $R_2 = CH_3$, Het=5-chloro-2-furanyl] was prepared from 6.6 g 5-chloro-2-trimethylstannylfuran (in turn prepared from 2chlorofuran and trimethyltin chloride in the presence of n-butyllithium), 9.0 g 5-[5-(2,6-dimethyl-4-iodophenoxy)pentyl]-3-methylisoxazole and 0.78 g dichlorobis(triphenylphosphine)palladium, and was obtained (4.4 g) as an off-white solid, m.p. 67–68° C. (from isopropyl acetate/hexane).

EXAMPLE 46

5-{5-[2,6-Dichloro-4-(5-chloro-2-furanyl)phenoxy]pentyl}-3-methylisoxazole [II; $R_1$ and $R_2 = Cl$, Het=5-chloro-2-furanyl] was prepared from 8 g 5-chloro-2-trimethylstannylfuran, 12 g 5-[5-(2,6-dichloro-4-iodophenoxy)pentyl]-3-methylisoxazole and 0.9 g dichlorobis(triphenylphosphine)palladium, and was obtained (6.2 g) as a tan solid, m.p. 59–60° C. (from isopropyl acetate/hexane).

EXAMPLE 47

5-{5-[2,6-Dichloro-4-(5-chloro-2-thienyl)phenoxy]pentyl}-3-methylisoxazole [II; $R_1$ and $R_2 = Cl$, Het=5-chloro-2-thienyl] was prepared from 5.3 g 5-chloro-2-trimethylstannylthiophene, 7.5 g of 5-[5-(2,6-dichloro-4-iodophenxoy)-pentyl]-3-methylisoxazole and 0.6 g dichlorobis(triphenylphosphine)palladium, and was obtained (6.1 g) as an offwhite solid, m.p. 53–55° C. (from isopropylacetate/hexane).

The compounds of the following Examples 48–52 where Het is a tetrazole moiety were prepared following the procedures of Examples 33 and 34 hereinabove:

EXAMPLE 48

(a) 5-{7-[4-(1H-Tetrazol-5-yl)phenoxy]heptyl}-3-methylisoxazole [I; $R = CH_3$, $R_1$ and $R_2 = H$, $Z = N$, $Y = (CH_2)_7$, Het=1H-tetrazolyl-5-yl], m.p. 151–153° C. (from 2-propanol), prepared from 5-[7-(4-cyanophenoxy)heptyl]-3-methylisoxazole and sodium axide in 65% yield.

The product of part (a) was caused to react with methyl iodide in the presence of potassium carbonate, and the product mixture was separated by chromotography to give the following isomeric products:

(b) 5-{7-[4-(2-Methyl-2H-tetrazol-5-yl)phenoxy]heptyl}-3-methylisoxazole [I; $R = CH_3$, $R_1$ and $R_2 = H$, $Z = N$, $Y = (CH_2)_7$, Het=2-methyl-2H-tetrazol-5-yl], m.p. 102–104° C. (from ethyl acetate/hexane) (29% yield).

(c) 5-{7-[4-(1-Methyl-1H-tetrazol-5-yl)phenoxy]heptyl}-3-methylisoxazole [I; $R = CH_3$, $R_1$ and $R_2 = H$, $Z = N$, $Y = (CH_2)_7$, Het=1-methyl-1H-tetrazol-5-yl], m.p. 84–86° C. (from ethyl acetate/hexane) (28% yield).

EXAMPLE 49

(a)

5-{5-[2,6-Dimethyl-4-(1H-tetrazol-5-yl)phenoxy]pentyl}-3-methylisoxazole [II; $R_1$ and $R_2$=$CH_3$, Het=1H-tetrazol-5-yl], m.p. 158–160° C. (from ethyl acetate), prepared from 5-[5-(2,6-dimethyl-4-cyanophenoxy)pentyl]-3-methylisoxazole (m.p. 50–51° C.) and sodium azide in 85% yield.

The product of part (a) was caused to react with methyl iodide in the presence of potassium carbonate, and the product mixture was separated by chromatography to give the following isomeric products:

(b) 5-{5-[2,6-Dimethyl-4-(2-methyl-2H-tetrazol-5-yl)phenoxy]pentyl}-3-methylisoxazole [II; $R_1$ and $R_2$=$CH_3$, Het=2-methyl-2H-tetrazol-5-yl], m.p. 63–65° C. (from ether) (57% yield).

(c) 5-{5-[2,6-Dimethyl-4-(1-methyl-1H-tetrazol-5-yl)phenoxy]pentyl}-3-methylisoxazole [II; $R_1$ and $R_2$=$CH_3$, Het=1-methyl-1H-tetrazol-5-yl], m.p. 65–67° C. (from ethyl acetate/ether) (24% yield).

EXAMPLE 50

5-{5-2,6-Dichloro-4-(1H-tetrazol-5-yl)phenoxy]pentyl}-3-methylisoxazole (Example 33) was caused to react with ethyl iodide in the presence of potassium carbonate, and the product mixture was separated by chromatography to give the following isomeric products:

(a) 5-{5-[2,6-Dichloro-4-(2-ethyl-2H-tetrazol-5-yl)phenoxy]pentyl}-3-methylisoxazole [II; $R_1$ and $R_2$=Cl, Het=2-ethyl-2H-tetrazol-5-yl], m.p. 34–36° C. (from ether/hexane) (52% yield).

(b) 5-{5-[2,6-Dichloro-4-(1-ethyl-1H-tetrazol-5-yl)phenoxy]pentyl}-3-methylisoxazole [II; $R_1$ and $R_2$=Cl, Het=1-ethyl-1H-tetrazol-5-yl], m.p. 62–64° C. (from ether) (5% yield).

EXAMPLE 51

5-{5-[2,6-Dimethyl-4-(1H-tetrazol-5-yl)phenoxy]pentyl}-3-methylisoxazole (Example 49a) was caused to react with ethyl iodide in the presence of potassium carbonate, and the product mixture was separated by chromatography to give the following isomeric products:

(a) 5-{5-[2,6-Dimethyl-4-(2-ethyl-2-H-tetrazol-5-yl)phenoxy]pentyl}-3-methylisoxazole [II; $R_1$ and $R_2$=$CH_3$, Het=2-ethyl-2H-tetrazol-5-yl], m.p. 56–57° C. (61% yield).

(b) 5-{5-[2,6-Dimethyl-4-(1-ethyl-1H-tetrazol-5-yl)phenoxy]pentyl}-3-methylisoxazole [II; $R_1$ and $R_2$=$CH_3$, Het=1-ethyl-1H-tetrazol-5-yl], m.p. 63–64° C. (from ether) (12% yield).

EXAMPLE 52

5-{5-[2,6-Dimethyl-4-(2-methoxycarbonylmethyl-2H-tetrazol-5-yl)phenoxy]pentyl}-3-methylisoxazole [II; $R_1$ and $R_2$=$CH_3$, Het=2-methoxycarbonylmethyl-2H-tetrazol-5-yl], m.p. 52–53° C. (from ether/hexane), was prepared from 5-{5-[2,6-dimethyl-4-(1H-tetrazol-5-yl)phenoxy]pentyl}-3-methylisoxazole (Example 49a) and methyl bromacetate in the presence of potassium carbonate (yield 61%).

EXAMPLE 53

5-{5-[2,6-Dimethyl-4-[2-(2-hydroxyethyl)-2H-tetrazol-5-yl]phenoxy]pentyl}-3-methylisoxazole [II; $R_1$ and $R_2$=$CH_3$, Het=2-(2-hydroxyethyl)-2H-tetrazol-5-yl].

A solution of 8.0 g 5-{5-[2,6-dimethyl-4-(2-methoxycarbonylmethyl-2H-tetrazol-5-yl)phenoxy]pentyl}-3-methylisoxazole (Example 52) in 50 ml tetrahydrofuran was added dropwise to a stirred suspension of 0.53 g lithium aluminum hydride in 250 ml dry tetrahydrofuran under nitrogen with cooling in an ice bath. The reaction mixture was allowed to come to room temperature and then treated with water and 15% sodium hydroxide. Isolation of the product provided 6.56 g (88%) of 5-{5-[2,6-dimethyl-4-[2-(2-hydroxyethyl)-2H-tetrazol-5-yl]phenoxy]pentyl}-3-methylisoxazole, m.p. 69–70° C. (from 2-propanol/hexane).

The same product can be obtained by alkylation of the compound of Example 49a with 2-hydroxyethyl bromide.

EXAMPLE 54

4-[3,5-Dimethyl-4-{[5-(3-methyl-5-isoxazolyl)pentyl]oxy}-phenyl]-1-methyl-1H-1,2,3-triazole [II; $R_1$ and $R_2$=$CH_3$, Het=1-methyl-1H-1,2,3-triazol-4-yl].

To a stirred solution of 6.6 ml diisopropylamine in 150 dry tetrahydrofuran at 0° C. under nitrogen was slowly added 18.4 ml (2.5 m) n-butyllithium. The mixture was cooled to −78° C., and 3.2 ml N-nitrosodimethylamine was then slowly added. The latter mixture was stirred for 30 min, and 6.0 g 5-[5-(2,6-dimethyl-4-cyanophenoxy)pentyl]-3-methylisoxazole in 33 ml dry tetrahydrofuran was added dropwise. The reaction mixture was stirred at −73° C. for 8.5 hours, and 3 ml glacial acetic acid in 10 ml tetrahydrofuran was then added. The reaction mixture was stirred overnight, then concentrated, and the residue dissolved in ethyl acetate. The solution was washed with water and saturated sodium chloride, dried over magnesium sulfate and concentrated to an oily residue. The latter was chromatographed on silica gel and eluted with ethyl acetate/hexane 60:40. The product was recrystallized from ethyl acetate/hexane to give 2.69 g 4-[3,5-dimethyl-4-{[5-(3-methyl-5-isoxazolyl)pentyl]oxy}phenyl]-1-methyl-1H-1,2,3-triazole, m.p. 117–118° C.

Biological evaluation of compounds of Formulas I and II has shown that they possess antiviral activity. They are useful in inhibiting virus replication in vitro and are primarily active against picornaviruses, including enteroviruses, polioviruses, echovirus and coxsackie virus, and especially numerous strains of rhinoviruses. The in vitro testing of the compounds of the invention against picornaviruses showed that viral replication was inhibited at minimum inhibitory concentrations (MIC) ranging from about 0.01 to about 5 micrograms per milliliter.

The MIC values were determined by a standard plaque reduction assay as follows: HeLa (Ohio) cells in monolayers were infected at a concentration of virus to give approximately 80 plaques per monolayer in the virus control (no drug present). The compound to be tested was serially diluted and included in the agar-medium overlay and in some cases, during the adsorption period as well. The MIC was determined to be that concentration of compound which reduced the number of plaques by 50% with respect to the untreated virus control.

In the standard test procedure, the compounds were tested against a panel of fifteen human rhinovirus (HRV) serotypes, namely HRV-2, -1A, -1B, -6, -14, -21, -22, -15, -25, -30, -50, -67, -89, -86 and -41. The MIC value for each rhinovirus serotype was determined, and the efficacy of each compound was determined in terms of $MIC_{50}$ and $MIC_{80}$ values, which is the concentration of the compound required to inhibit 50% and 80%, respectively, of the tested serotypes.

The following Table gives the testing results with the compounds of the invention. For some of the compounds, the $MIC_{50}$ and $MIC_{80}$ values are based on the testing of fewer than 15 rhinovirus serotypes. In these cases the number of serotypes (N) is indicated in parentheses after the $MIC_{80}$ figure.

TABLE

| Example No. | MIC (Polio 2) | $MIC_{50}$ (Rhinovirus) | $MIC_{80}$ (N) (Rhinovirus) |
|---|---|---|---|
| 1(c) | 2.5 | 0.15 | 0.44 |
| 2(b) | 0.02 | 0.3 | 0.55 |
| 3(b) | IA | 0.27 | 0.4 |
| 4 | 0.05 | | 2.56 (1) |
| 5(b) | 0.02 | 0.17 | 1.33 |
| 6(c) | 1.0 | 0.16 | 0.57 |
| 7(b) | IA | 1.12 | 27.1 (6) |
| 9 | 0.9 | 0.3 | 0.94 |
| 10(c) | 2.24 | 0.25 | 0.91 |
| 11(d) | 3.1 | 0.19 | 0.97 |
| 13(b) | 3.0 | 0.76 | 0.26 |
| 14 | 6.2 | 0.15 | 0.5 |
| 15(b) | IA | 0.13 | 1.15 |
| 16 | IA | 0.27 | 1.1 |
| 17(b) | IA | 0.1 | 0.94 |
| 19(b) | IA | 0.285 | 25.65 (6) |
| 20(b) | 4.4 | 0.23 | 0.7 |
| 21(b) | IA | 0.08 | 0.8 |
| 22 | IA | 0.15 | 1.14 |
| 23(b) | IA | 1.09 | 99 (a) (6) |
| 24 | IA | 0.38 | 1.6 |
| 25(b) | IA | 0.14 | 0.82 |
| 26 | IA | 0.12 | 0.54 |
| 27(b) | IA | 1.33 | 99 (a) (6) |
| 28(b) | IA | 0.22 | 0.67 |
| 29 | IA | 0.38 | 25.33 (6) |
| 30(b) | 4.9 | 1.4 | 2.03 |
| 31(b) | 0.06 | 0.48 | 1.2 |
| 32(c) | IA | 0.23 | 0.91 |
| 34 (1st compd.) | 2.9 | 0.07 | 0.1 |
| (2nd compd.) | IA | 1.28 | 2.79 |
| 35(b) | 0.09 | 50.8 | 99 (a) (2) |
| 36 | 2.24 | IA | IA (2) |
| 37(b) | 5.3 | 0.8 | 99 (a) (6) |
| 38 | IA | 2 | 99 (a) (7) |
| 39 | — | 54.7 | 99 (a) (2) |
| 40 | | 0.76 | 26.85 (6) |
| 41 | — | 49.6 | 99 (a) (6) |
| 42 | IA | 1.52 | 99 (a) (6) |
| 43 | — | 0.14 | 0.78 |
| 44 | — | 0.15 | 0.96 |
| 45 | 12.5 | 0.25 | 0.34 |
| 46 | IA | 0.34 | 0.7 |
| 47 | IA | 0.43 | 1.35 |
| 48(b) | IA | 0.24 | 27.1 (6) |
| 48(c) | 1.37 | 50 | 99 (a) (2) |
| 49(b) | IA | 0.14 | 0.168 |
| 49(c) | IA | 1.83 | 2.86 (2) |
| 50(a) | — | 0.04 | 0.13 |
| 50(b) | — | 1.15 | 1.6 (2) |
| 51(a) | — | 0.069 | 0.24 |
| 51(b) | — | 1.4 | 3 |
| 52 | IA | IA | IA |
| 53 | — | 0.856 | 1.68 (2) |
| 54 | IA | 0.58 | 2.22 (6) |

IA = Inactive at dose levels tested
(a) = Inactive against more than 20% of the serotypes tested The compound of Example 49(b), namely 5-{5-[2,6-dimethyl-4-(2-methyl-2H-tetrazol-5-yl)phenoxy]pentyl}-3-methylisoxazole, was also found to be active against 27 human enteroviruses ($MIC_{80}$=3.2 μg/ml). (In vivo efficacy studies in mouse infection models showed that this compound had potent oral activity in echovirus-9 and coxsackie virus A-9 infections; the $PD_{50}$ in coxsackie virus A-9 infected mice was 2.0 mg/kg. The compound was also effective against echovirus type-9 induced paralysis in mice with twice a day dosing with 1.5 mg/kg.

The antiviral compositions are formulated for use by preparing a dilute solution or suspension in a pharmaceutically acceptable aqueous, organic or aqueousorganic medium for topical or parenteral administration by intravenous or intramuscular injection, or for intranasal or ophthalmic application; or are prepared in tablet, capsule, or aqueous suspension form with conventional excipients for oral administration.

We claim:

1. A compound of the formula:

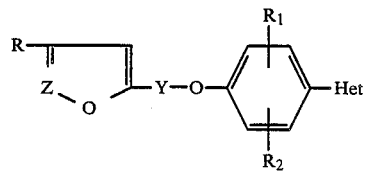

wherein:
Y is an alkylene bridge of 3–9 carbon atoms; Z in N; R is lower-alkyl of 1–5 carbon atoms;
$R_1$ and $R_2$ are hydrogen, halogen, lower-alkyl, lower-alkoxy, nitro, lower-alkoxycarbonyl or trifluoromethyl; and
Het is selected from the group consisting of:

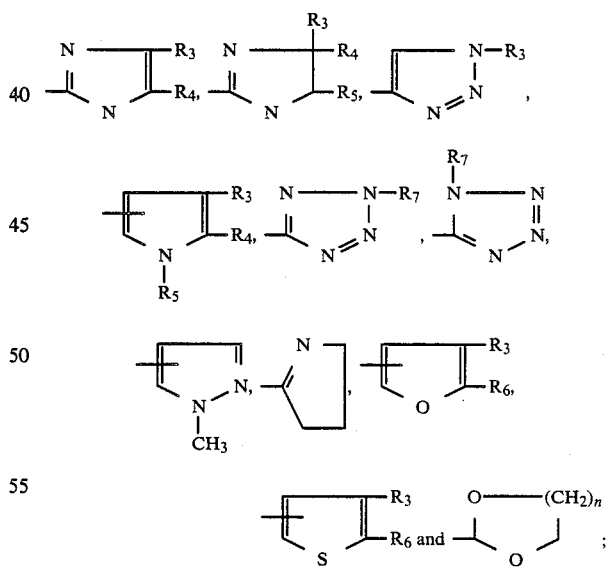

where n is 2 or 3; and
$R_3$, $R_4$ and $R_5$ are hydrogen or lower-alkyl of 1–5 carbon atoms;
$R_6$ is hydrogen, lower-alkyl of 1–5 carbon atoms or chloro;
$R_7$ is hydrogen, or alkyl or hydroxyalkyl of 1–5 carbon atoms; or pharmaceutically acceptable acid-addition salts of basic members thereof.

2. A compound according to claim 1 of the formula

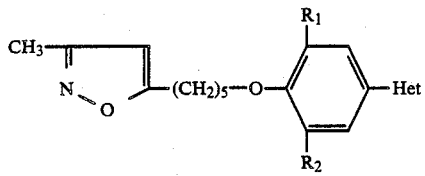

wherein $R_1$, $R_2$ and Het have the meanings given in claim 1.

3. A compound according to claim 2 wherein Het is a furanyl group.

4. 5-{5-[2,6-Dichloro-4-(2-furanyl)phenoxy]pentyl}-3-methylisoxazole, according to claim 3.

5. 5-{5-[2,6-Dimethyl-4-(5-methyl-2-furanyl)phenoxy]pentyl}-3-methylisoxazole, according to claim 3.

6. A compound according to claim 2 wherein Het is a thienyl group.

7. 5-{5-[2,6-Dichloro-4-(2-thienyl)phenoxy]pentyl}-3-methylisoxazole, according to claim 6.

8. A compound according to claim 2 wherein Het is a tetrazolyl group.

9. 5-{5-[2,6-Dichloro-4-(2-methyl-2H-tetrazol-5-yl)phenoxy]pentyl}-3-methylisoxazole, according to claim 8.

10. 5-{5-[2,6-Dimethyl-4-(2-methyl-2H-tetrazol-5-yl)phenoxy]pentyl}-3-methylisoxazole, according to claim 8.

11. 5-{5-[2,6-Dichloro-4-(2-ethyl-2H-tetrazol-5-yl)phenoxy]pentyl}-3-methylisoxazole, according to claim 8.

12. 5-{5-[2,6-Dimethyl-4-(2-ethyl-2H-tetrazol-5-yl)phenoxy]pentyl}-3-methylisoxazole, according to claim 8.

13. A composition for combating picornaviruses which comprises an antivirally effective amount of a compound according to claim 1, in admixture with a suitable carrier or diluent.

14. A composition according to claim 13 for combating rhinoviruses.

15. A composition according to claim 14 wherein the antivirally effective compound is 5-{5-[2,6-dichloro-4-(2-methyl-2H-tetrazol-5-yl)phenoxy]pentyl}-3-methylisoxazole.

16. A composition according to claim 14 wherein the antivirally effective compound is 5-{5-[2,6-dimethyl-4-(2-methyl-2H-tetrazol-5-yl)phenoxy]pentyl}-3-methylisoxazole.

17. A method for combating picornaviruses which comprises contacting the locus of said viruses with a compound according to claim 1.

18. A method according to claim 17 for combating rhinoviruses.

19. A method according to claim 18 wherein the compound used is 5-{5-[2,6-dichloro-4-(2-methyl-2H-tetrazol-5-yl)phenoxy]pentyl}-3-methylisoxazole.

20. A method according to claim 18 wherein the compound used is 5-{5-[2,6-dimethyl-4-(2-methyl-2H-tetrazol-5-yl)phenoxy]pentyl}-3-methylisoxazole.

21. A method for combating an picornaviral infection in a mammalian host which comprises administering to said host an antivirally effective amount of a compound according to claim 1.

* * * * *